United States Patent [19]
Lee

[11] 3,966,967
[45] June 29, 1976

[54] COMPOSITIONS AND METHODS OF TREATING PSORIASIS WITH VINYLOGS OF DESMETHYL RETINOIC ACID

[75] Inventor: Kwan-Hua Lee, San Francisco, Calif.

[73] Assignee: The Regents of the University of California, Berkeley, Calif.

[22] Filed: Oct. 29, 1974

[21] Appl. No.: 518,548

Related U.S. Application Data

[60] Division of Ser. No. 343,559, March 21, 1973, Pat. No. 3,882,244, and a continuation-in-part of Ser. No. 207,623, Dec. 13, 1971, abandoned.

[52] U.S. Cl................................ 424/318; 424/344
[51] Int. Cl.² ....................................... A61K 31/07
[58] Field of Search ............................... 424/318

[56] References Cited
UNITED STATES PATENTS

3,689,667  9/1972  Lee ................................... 424/318

OTHER PUBLICATIONS

Frost et al., Jama. 207, No. 10, (3/10/69) pp. 1863–1868.
Fry et al., British J. of Dermatology, vol. 83, (1970), pp. 391–396.
Fredriksson, Dermatologica 142, (1971), pp. 133–136.
Orfands, et al., British J. of Dermatology (1973), pp. 167–182.

*Primary Examiner*—Norman A. Drezin
*Attorney, Agent, or Firm*—Townsend and Townsend

[57] ABSTRACT

The C20 and C22 vinylogs of desmethyl retinoic acid have been found highly effective in promoting wound healing, in the treatment of acne, psoriasis and related skin disorders. The acid is applied to the site as a solution, ointment or powder. These acids are the most effective yet found for such purposes yet do not have some of the undesirable side effects of retinoic acid.

2 Claims, No Drawings

COMPOSITIONS AND METHODS OF TREATING PSORIASIS WITH VINYLIGS OF DESMETHYL RETINOIC ACID

REFERENCE TO RELATED APPLICATION

This is a division of application Ser. No. 343,599, filed Mar. 21, 1973, now U.S. Pat. No. 3,882,244.

This application is a continuation-in-part of my application Serial Number 207,623, filed December 13, 1971, now abandoned.

SUMMARY OF THE INVENTION

In accordance with the present invention it has been found that certain desmethyl vinylogs of retinoic acid are highly effective in healing wounds and treating skin disorders such as psoriasis and acne. The mechanisms involved in the healing of acne and psoriasis are not understood but it has been found that the compounds of the present invention are highly effective in the treatment of these disorders. It has also been found that the compounds of the present invention are highly effective in wound healing.

Inflammation and mucopolysaccharide synthesis are the two important features in the early stage of wound healing. The term "wound" as used in this application means any topical lesion such as a surgical incision, accidental wound or ulcer. Aspirin inhibits both features. The healing inhibitory action of aspirin and other inflammatory agents has been demonstrated. Vitamin A increases mucopolysaccharide synthesis and it also causes inflammation. The ability of vitamin A alone to promote healing and its effectiveness in reversing the healing retardation action of aspirin is known. Retinoic acid (the acid form of vitamin A) and its salts also have been found active compounds in promoting healing. Topical application of retinoic acid or its salts reverses the healing retardation action caused by oral administration of sodium salicylate, prednisone and other anti-inflammatory agents and topical application of salicylic acid or hydrocortisone. Topical application of retinoic acid and its salts promotes skin wound healing in rats and human beings.

Retinoic acid has been used in the treatment of psoriasis, acne, and related dermatological conditions such as Darier's disease, ichthyosis, hyperkeratoses, pityriasis, and pseudofolliculitis of the beard. The exact mechanism of action of retinoic acid is unknown; however, the "normalizing" effect on keratinization that occurs is seen concomitantly with irritation which is characterized by redness and peeling of the skin. In fact, it is believed that retinoic acid may have to be irritating to be effective in acne. In psoriasis, the beneficial action of retinoic acid is limited by its irritant effect. Additionally, most of the other agents used to treat psoriasis—antimetabolites, tars, anthralin—are not used more frequently because of their potential for irritation.

It has now been found that 2,6,6,-Trimethyl-1-(10'-carboxy-deca-1',3',5',7',9'-pentaenyl) cyclohex-1-ene acid and 2, 6, 6,-Trimethyl-1-(12'-carboxy-dodeca-1',-3',5',7',11'-hexaenyl)cyclohex-1-ene acid are even more effective than vitamin A or vitamin A acid for wound healing. The corresponding C16 and C18 acids have also been made and tested but they are considerably less effective for this condition than the C20 and C22 acids of the present invention. These latter compounds have been shown to be effective in the treatment of psoriasis, acne, and related skin conditions. Furthermore, the acids of the present invention have been found to be considerably less toxic and have fewer side effects, even when used at higher concentrations than retinoic acid.

It is very practical to dust these compounds on the body or to apply either of them as a solution or in an ointment. The C20 acid is preferred.

DESCRIPTION OF THE PREFERRED EMBODIMENTS

The topical application of C20 or C22 acids has been found to promote wound healing. This is true both of animals which have not been otherwise treated and also true of animals which have been treated with anti-inflammatory agents such as a salicylate, hydrocortisone, prednisone, indomethacin, mefenamic acid and the like. These compounds normally retard healing and C20 and C22 acids reverse this action. The C20 and C22 acids also are effective agents in the treatment of psoriasis and acne.

PREPARATION OF THE COMPOUNDS

The following is one method of preparing the novel C20 and C22 acids of the present invention. In the synthesis selected, beta ionone is first converted to an aldehyde having 16 carbon atoms and this is reacted with triethylphosphonocrotonate to produce the C20 ethyl ester and this is hydrolyzed to the desired C20 acid. It is also possible to go directly from the C12 aldehyde to the C20 ester by employing a phosphono compound having eight carbon atoms with conjugated double bonds. One route for preparing the C22 acid is through the C20 acid.

PREPARATION OF BETA C12 ACID

At 0° pass 84 grams of chlorine gas into 400 ml of 10M sodium hydroxide solution. To which, at room temperature, add 64 grams of beta ionone. Stir for 3 hours. Add 80 ml of methanol and maintain the temperature below 85°C by adding crushed ice and then bring the pH to about 4 by adding phosphoric acid. Cool to room temperature and the beta C12 acid will rise to the surface and can be filtered with the aid of suction. The crude acid is then dissolved in 20% aqueous sodium hydroxide solution and extracted with ether. The aqueous solution is acidified with phosphoric acid and again extracted with ether. The ether extract is dried with anhydrous magnesium sulfate. The ether is evaporated and the acid is recrystallized from 70% methanol solution to provide the purified C12 acid.

PREPARATION OF C12 ALCOHOL

Ten grams of lithium aluminum hydride is placed in a 3 necked flask under a nitrogen atmosphere and 50 ml of anhydrous ethyl ether is added and stirred with a magnetic stirrer at −15°C. Dissolve 50 grams of the C12 acid previously prepared in anhydrous ether and add slowly into the flask containing the lithium aluminum hydride. The temperature should be maintained below minus 10°C. After all of the acid has been added, the temperature can be allowed to rise to room temperature and kept at this temperature for 1 hour. The mixture is then cooled to 0° and 1N sulphuric acid is added until bubbles cease to form. The temperature should be maintained below 5°C. The reaction mixure is filtered and the precipitate washed with ether. The ether layer is separated and washed with water and is then dried with anhydrous magnesium sulfate and the ether evaporated. The yield is about 93% of theory.

PREPARATION OF C12 ALDEHYDE

In the following reaction, activated manganese dioxide is used which can be prepared either by the method of Attenburrow et al J. Chem. Soc. 1094 (1952) or Carpino, J. Org. Chem. Vol. 35 No. 11 (1970) 3971.

About 50 grams of the C12 alcohol in CCl$_4$ solution is placed in a dropping funnel attached to a two-liter flask. 500 grams of activated manganese dioxide and 1000 ml of anhydrous carbon tetrachloride are placed in the flask and stirred. The C12 alcohol solution is now slowly run into the manganese dioxide suspension and stirring is continued at room temperature for 2 hours after all of the alcohol has been added. The mixture is filtered and washed with carbon tetrachloride and the extract is then dried and evaporated. The yield is about 95% of theory.

PREPARATION OF C16 ESTER

Weigh 47 grams of a sodium hydride in oil dispersion (57% NaH) and place it in a two-liter flask. Wash with anhydrous ether. Add 1000 ml of anhydrous tetrahydrofuran (THF) and cool to zero. One then places 140 grams of triethylphosphonocrotonate in a dropping funnel and adds it dropwise to the sodium hydride suspension with stirring. Stirring is continued at zero degrees for ½ hour after all the crotonate has been added. About 50 grams of the C12 aldehyde dissolved in THF is now slowly added and warmed to room temperature and allowed to stand at room temperature over ½ hour. The mixture is then cooled to zero and one adds a saturated sodium chloride solution to destroy the excess of sodium hydride. The mixture is now extracted with petroleum ether and the extract dried to evaporate the solvent, yielding the desired ester.

PREPARATION OF C16 ACID

The ester is hydrolyzed by refluxing it in a 10% potassium hydroxide-ethanol solution under nitrogen for 4 hours. The mixture contains 50 grams of the ester, 50 grams of potassium hydroxide, 300 ml of water and 200 ml of ethanol. After the hydrolysis is completed, acidify the mixture. The acid can be extracted with ethyl ether.

PREPARATION OF C20 AND C22 ACIDS

The detailed procedure for obtaining the C20 from the C16 acid is not given since the reactions are substantially the same as outlined above. The C16 acid recovered from the last step is converted to the alcohol, utilizing lithium aluminum hydride and this is converted to the corresponding aldehyde utilizing manganese dioxide as described above. The aldehyde now is reacted with triethylphosphonocrotonate to produce the C20 ethyl ester and this in turn is hydrolyzed as described above to produce the C20 acid of the present invention. The C22 acid can be prepared from the C20 acid by using the above method and employing the triethylphosphonoacetate.

C20 or C22 acids can be applied in the form of an ointment, as a solution in oil or as a powder. In each instance a concentration of about 0.1% has been found suitable although larger or smaller concentrations may be used. Below about 0.01%, the effectiveness falls off and increasing the concentration to 1 to 2% increases the effectiveness only slightly; a concentration of about 0.1%, whether in an ointment, oil solution or powder, is about optimum.

Suitable oil carriers include physiologically acceptable oils in which the acid is soluble such as isopropyl myristate, corn oil, cottonseed oil and the like. Powder can be prepared utilizing the C20 or C22 acid crystals by grinding the crystals with a suitable inert carrier such as talc. C20 or C22 acid can be combined with any of the usual ointment bases used in pharmacy. One suitable base is known as NIB (non-ionic base) developed by the University of California School of Pharmacy and a suitable formulation has the following approximate composition:

| | |
|---|---|
| C22 acid | 2% |
| Cetyl alcohol | 6 |
| Stearly alcohol | 6 |
| White petrolatum | 14 |
| Liquid petrolatum | 20 |
| Methyl paraben | 0.15 |
| Propyl paraben | 0.06 |
| Polysorbate 80 | 1.5 |
| Polyoxyl 40 stearate | 5 |
| Propylene glycol | 2 |
| Purified water | q.s. 100% |

Other suitable cream, gel and lotion bases that can be formulated follow:

| Cream base | % wt/wt |
|---|---|
| C20 acid | 1.0 |
| Ethyl alcohol | 10.0 |
| Thimerosal | 0.01 |
| Stearic acid | 17.0 |
| Potassium carbonate | 1.0 |
| Glycerine | 5.0 |
| Tocopherol | 0.1 |
| Purified water | q.s. 100% |

| Gel base | % wt/wt |
|---|---|
| Carbopol 940 | 1.0 |
| Thimerosal | 0.01 |
| Sodium hydroxide | 0.4 |
| C20 acid | 0.1 |
| Ethyl alcohol | 10.0 |
| Polysorbate 80 | 2.0 |
| Butylated hydroxy toluene | 0.02 |
| Purified water | q.s. 100% |

| Lotion base | % wt/wt |
|---|---|
| Ethyl alcohol | 50 |
| C22 acid | 0.01 |
| Butylated hydroxy toluene | 0.02 |
| Propylene glycol | q.s. 100% |

USE OF COMPOUNDS IN WOUND HEALING

Gridlay and Waugh (Arch. Surg. 63, 288 (1951) used granuloma formation induced by polyvinyl sponge to study tissue regeneration. Since then this method has been used as a standard method to study would healing. Dunphy and his associates (Ann. N.Y. Acad. Sci. 86, 943 (1960) have pointed out that the repairment of connective tissue is the most basic feature in wound healing, and they used granuloma formation techniques in their many wound healing studies.

This method involves subcutaneous implantation of cotton-pellets and measuring the size of the granuloma induced after a few days. Anti-inflammatory agents reduce the size or weight of granuloma as compared with that of the control. Those compounds which promote healing increase the size or weight of the granuloma.

Growth of granulation tissue into cotton-pellets was induced by subcutaneous implantation at two symmetrical dorsolateral sites of Sprague-Dawley male rats weighing 120 ± 5 g under ether anesthesia.

The cotton-pellet implanted on the right side contains the compound under test and the cotton-pellet implanted on the left side serves as the control. The compound was introduced to the pellet as its ether solution. The ether was completely evaporated before implantation. On the seventh day after implantation, the animals were killed with ether and the body weights were taken. The granulomas were carefully removed and weighed rapidly on a torsion balance. After drying in an oven at 65°C for 48 hours the dried slices were weighed. The following results were obtained.

tration in a base consisting of 50% propylene glycol and 50% ethanol. The following results were obtained:

C20 vs RETINOIC ACID

| Subject | 1 Week | 2 Weeks | 3 Weeks | Comment |
|---|---|---|---|---|
| 1 | no effect | R>C20 | R=C20 | 25% improvement |
| 2 | R>C20 | C20>R | C20>R | 75% improvement |
| 3 | no effect | no effect | C20>R | 25% improvement |
| 4 | R>C20 | R=C20 | C20>R | 50% improvement |
| 5 | R=C20 | C20>R | C20>R | 75% improvement |

It was concluded that the C20 acid of the present invention had substantially greater effectiveness in most instances than retinoic acid. The compound of the present invention did appear to act more slowly than EFFECT OF 3',7'-DESMETHYL RETINOIC ACID VINYLOGS ON COTTON-PELLET INDUCED GRANULOMA IN RATS

| Group | No. of Animals | Acids Applied | Granuloma Wet Wt. mg. Expt. Control | Expt. Control | Granuloma Dry Wt. mg. Expt. Control | Expt. Control |
|---|---|---|---|---|---|---|
| I | 6 | A | 238.6±12.1 | | 29.0±2.1 | |
| | | | 220.5±12.2 | 1.1 | 27.2±2.1 | 1.1 |
| II | 14 | B | 331.1±14.8 | | 43.1±2.6 | |
| | | | 208.8± 5.9 | 1.5 | 25.5±1.5 | 1.7 |
| III | 43 | C | 430.2± 8.1 | | 68.9±1.5 | |
| | | | 205.0± 2.7 | 2.2 | 23.9±0.9 | 2.9 |
| IV | 30 | D | 373.9± 8.6 | | 60.5±1.6 | |
| | | | 202.9± 4.6 | 1.8 | 24.9±1.2 | 2.4 |

A Acid: 2,6,6,-Trimethyl-1-(6'-carboxy-hexa-1',3',5'trienyl) cyclohex-1-ene.
B Acid: 2,6,6,-Trimethyl-1-(8'-carboxy-octa-1',3',5',7'tetraenyl) cyclohex-1-ene or 3',7'-desmethyl retinoic acid.
C Acid: 2,6,6,-Trimethyl-1-(10'-carboxy-deca-1',3',5',7',9'-pentaenyl) cyclohex-1-ene.
D Acid: 2,6,6,-Trimethyl-1-(12'-carboxy-dodeca-1',3',5',7',9',11'hexaenyl) cyclohex-1-ene.

It is believed apparent from the foregoing that the C20 and C22 acids of the present invention (Acids C and D in the table) are highly effective for wound healing and are much more effective then the homologs having 16 or 18 carbon atoms. The C20 acid is somewhat more effective than the C22 acid.

Further tests established that the C20 and C22 acids are not toxic or at least not as toxic as retinoic acid. Retinoic acid inhibits embryonic chick tibia growth while C20 and C22 do not. Retinoic acid, at higher dosage (4 mg/100 g rat) inhibits growth. The C20 at even higher dosages (8 mg/100g rat) does not inhibit growth.

USE OF COMPOUNDS IN TREATMENT OF PSORIASIS

The following tests were made to show the effectiveness of these compounds in the treatment of chronic psoriasis. Five patients were utilized; each of the patients had a history of chronic stable psoriasis which had proved more or less resistant to topical steroid therapy. In this series of tests, the C20 acid of the present invention was compared with retinoic acid (designated R in the table) and the test agents were applied to one or two equivalently matched lesions on opposite sides, three times daily for three weeks. No other therapy was utilized. At the end of each week an experienced therapist made an evaluation of the relative effectiveness of each of the agents being tested. The compounds under test were applied in 0.02% concentration retinoic acid, since after one week those lesions treated with retinoic acid appeared to be more improved. However, at the conclusion of the tests, four out of the five subjects of the C20 acid of the present invention were clearly superior to retinoic acid while in one instance it was equal to it.

USE OF COMPOUNDS IN THE TREATMENT OF ACNE

In another series of tests the comedolytic effect of the C20 acid of the present invention was compared with that of retinoic acid. In this series of tests, rabbits were employed as a test model. The comedogenic property of various chemicals on rabbit ears has been demonstrated by Kligman (Arch. Derm., Vol. 98, July, 1968, pp. 53 and 58). This acneigenic effect parallels that in human skin and may be reduced by effective anti-acne drugs. Thus, this animal model has served as a reliable screen for agents that may be used to reduce comedones in human acne.

The ears of rabbits were treated for two weeks with 10% crude coal tar, which produced comedones (distension of the follicles with impacted horn) very similar to that in human acne. Without treatment, these comedones do not change over the next two weeks. Concentrations of 0.1% and 0.025% of the compound in 50% propylene glycol/50% ethanol were applid once daily for a period of 2 weeks. After 2 weeks of treatment, the experienced observer can estimate the degree of reduction in size of the impaction that has been achieved.

The degree of healing was scored on a scale of five wherein Zero equaled no change, one equaled a slight decrease, two equaled a moderate decrease, three equaled a great decrease, and 4 equaled complete abolition of comedones. The following data were obtained:

|  | C20 vs RETINOIC ACID | | |
|---|---|---|---|
| Rabbit | Concentration | C20 | Retinoic Acid |
| 1 | 0.1% | 3 | 3 |
| 2 | 0.1% | 3 | 3 |
| 3 | 0.1% | 3 | 2 |
| 4 | 0.025% | 2 | 2 |
| 5 | 0.025% | 3 | 3 |
| 6 | 0.025% | 2 | 2 |

It will be seen from these data that in each instance the C20 acid was at least as effective as retinoic acid and in some instances it was substantially better. However, it did have a great advantage in that it was less irritating. Retinoic acid produces erythema and scaling in the rabbit ear; histologically an infiltration by neutrophiles can be observed. The C20 compound of the present invention was grossly and histologically less irritating to the tissue. Normally in itself the retinoic acid is not very effective in the treatment of acne unless it produces peeling and redness. The compound of the present invention has the healing effect of retinoic acid without the irritation effects.

I claim:

1. A medicine for topical application to the body comprising a physiological acceptable carrier and from about 0.1 to 2% of 2, 6, 6,-Trimethyl-1-(10'-carboxy-deca-1',3',5',7',9'-pentaenyl) cyclohex-1-ene.

2. A method of treating a psoriasis comprising: applying topically to the affected area of a patient having psoriasis, an amount effective for treating said psoriasis, of 2,6,6-trimethyl-1-(10'-carboxy-deca-1',3',5',7',9'-pentaenyl)cyclohex-1-ene in combination with a physiologically acceptable carrier.

* * * * *